United States Patent
Chuang

(10) Patent No.: US 8,831,232 B2
(45) Date of Patent: Sep. 9, 2014

(54) ANTI-NOISE EARMUFF DEVICE WITH BLUETOOTH MODULE AND AUDIO SIGNAL PROCESSOR

(76) Inventor: Ching Kuo Chuang, New Taipei (TW)

(*) Notice: Subject to any disclaimer, the term of this patent is extended or adjusted under 35 U.S.C. 154(b) by 349 days.

(21) Appl. No.: 13/232,463

(22) Filed: Sep. 14, 2011

(65) Prior Publication Data

US 2013/0064378 A1     Mar. 14, 2013

(51) Int. Cl.
*A61F 11/06* (2006.01)
*H04R 5/00* (2006.01)

(52) U.S. Cl.
CPC . *A61F 11/06* (2013.01); *H04R 5/00* (2013.01)
USPC .............................. 381/28; 381/72

(58) Field of Classification Search
USPC .............. 381/72, 119–120, 104, 311, 315
See application file for complete search history.

(56) References Cited

U.S. PATENT DOCUMENTS

| | | | | |
|---|---|---|---|---|
| 6,961,436 B1* | 11/2005 | Han | ............................. | 381/104 |
| 7,248,706 B2 | 7/2007 | Chuang | | |
| 7,548,617 B2* | 6/2009 | Yuen | ............................. | 379/430 |
| 2005/0213782 A1* | 9/2005 | Miller et al. | .................. | 381/110 |
| 2009/0112589 A1* | 4/2009 | Hiselius et al. | ................ | 704/246 |
| 2012/0045994 A1* | 2/2012 | Koh et al. | ..................... | 455/41.3 |
| 2012/0051561 A1* | 3/2012 | Cohen et al. | .................. | 381/122 |

* cited by examiner

*Primary Examiner* — Duc Nguyen
*Assistant Examiner* — Phan Le
(74) *Attorney, Agent, or Firm* — Ming Chow; Sinorica, LLC

(57) ABSTRACT

An anti-noise earmuff device includes an audio signal processor unit, a Bluetooth module, an audio mixer unit and an amplifier unit. The audio signal processor unit is arranged in the earmuffs for control audio signal output, protecting the user's eardrums against noise of high-decibel level. The Bluetooth module receives or communicates with a mobile communication device through an antenna, allowing the user to listen to the music and to communicate with people outside without needing taking off the earmuff device.

6 Claims, 3 Drawing Sheets

ANTI-NOISE EARMUFF DEVICE WITH BLUETOOTH MODULE AND AUDIO SIGNAL PROCESSOR

BACKGROUND OF THE INVENTION

1. Field of the Invention

The present invention relates to earmuffs for protecting the ears against noises and more particularly, an anti-noise earmuff device that has built therein a Bluetooth module and an audio-signal processor.

2. Description of the Related Art

When shooting or working in an extremely high noisy place, people would wear earmuffs to obstruct unbearable noise in order not to get their eardrums hurt.

U.S. Pat. No. 7,248,706 discloses an audio signal detecting device, which is to be disposed in a user's earmuffs for protecting his eardrums against noise of high-decibel level. This design is functional; however, it is not equipped with any personal communication or audio transmission system. Thus, special arrangement must be added so that the user can enjoy listening to music or communication with outside people without needing taking off the earmuffs.

Further, a conventional Bluetooth communication device is not practical for use under a noisy environment, for example, a shooting place, for communication with the shooter. Further, when a shooter in a shooting place is not shooting and going to listen to the music or to pick up a cell phone, the shooter must take of the earmuffs. Thus, the use of conventional earmuffs is somewhat inconvenient in applications.

SUMMARY OF THE INVENTION

The present invention has been accomplished under the circumstances in view. It is the main object of the present invention to provide an anti-noise earmuff device, which has built therein an audio signal processor that processes inputted audio signals to get attenuated to below 79 db, protecting the user's eardrums against noise of high-decibel level.

It is another object of the present invention to provide an anti-noise earmuff device, which allows the user to listen to the music and to communicate with people outside without needing taking off the earmuff device.

To achieve these and other objects of the present invention, an anti-noise earmuff device comprises: at least one audio signal processor unit adapted for receiving external audio signals; an audio mixer unit electrically coupled with the at least one audio signal processor unit and adapted for receiving and processing the audio signals outputted by the at least one audio signal processor unit; an amplifier unit electrically coupled with the audio mixer unit and adapted for receiving and amplifying the audio signals outputted by the audio mixer unit; and a Bluetooth module electrically coupled with the audio mixer unit.

Further, each audio signal processor unit consists of an audio receiver, a primary amplifier circuit, a secondary amplifier circuit, a current amplifier circuit, a wave detection circuit, a switch circuit and a regulator circuit.

Further, the audio receiver can be a capacitive microphone.

Further, the switch circuit can be a transistor or diode.

Further, the regulator circuit can be a variable resistor.

Further, the audio mixer unit consists of a left channel mixer and a right channel mixer.

Further, the amplifier unit consists of a left audio amplifier and a right audio amplifier.

Further, the Bluetooth module comprises a sound volume control circuit consisting of an antenna, a Bluetooth microphone and a variable resistor, and is electrically coupled with the left channel mixer and right channel mixer of the audio mixer unit.

DETAILED DESCRIPTION OF THE PREFERRED EMBODIMENT

Figure 1:
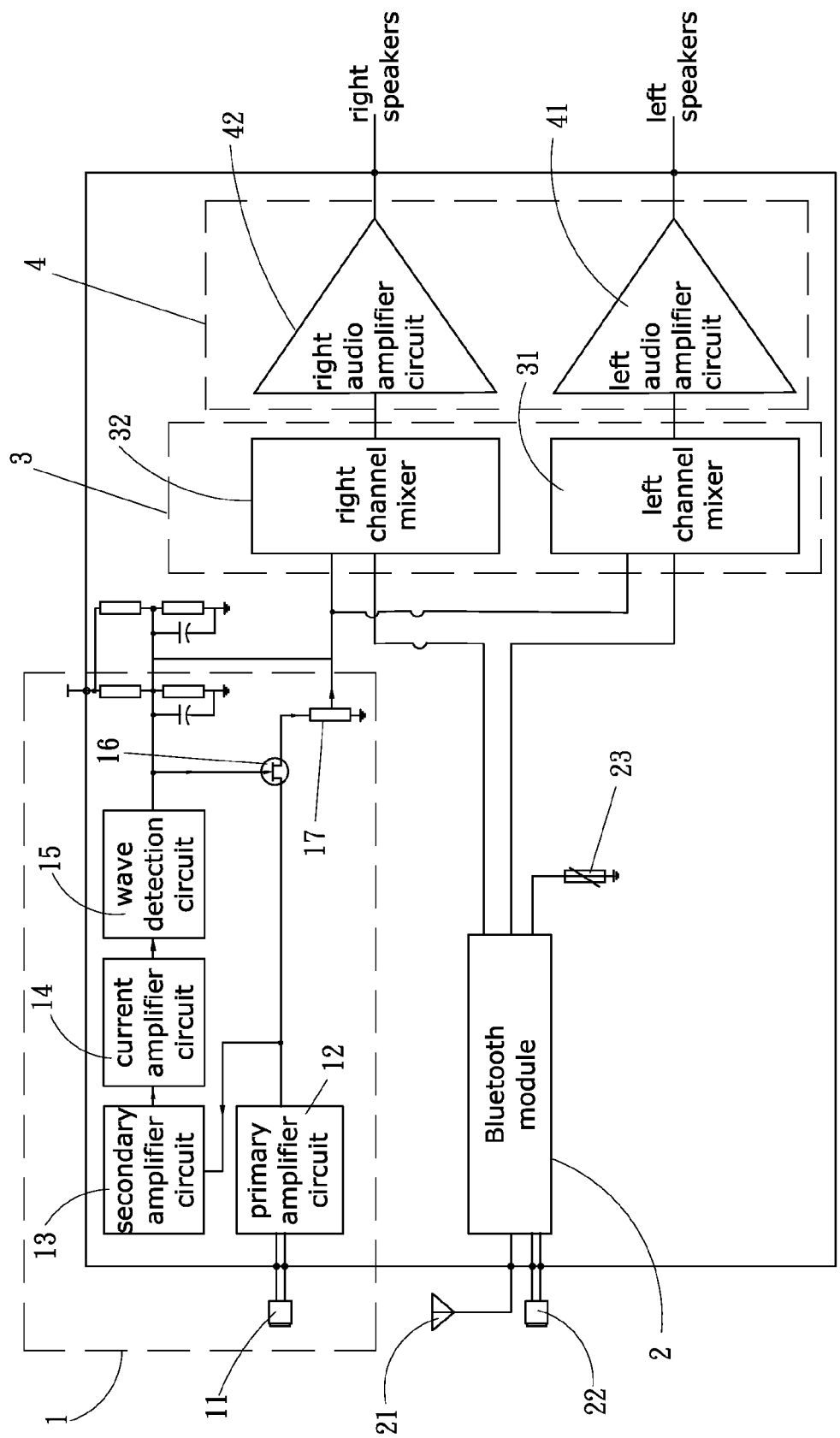
FIG. 1 is a system block diagram of an anti-noise earmuff device in accordance with a first embodiment of the present invention.

Referring to FIG. 1, an anti-noise earmuff device in accordance with a first embodiment of the present invention is shown having built in the muffs (not shown) thereof an audio signal processor unit 1, a Bluetooth module 2, an audio mixer unit 3 and an amplifier unit 4.

The audio signal processor unit 1 comprises an audio receiver 11, a primary amplifier circuit 12, a secondary amplifier circuit 13, a current amplifier circuit 14, a wave detection circuit 15, a switch circuit 16 and a regulator circuit 17. The audio receiver 11 is a capacitive microphone for receiving external audio signals. The primary amplifier circuit 12 is adapted for amplifying audio signals received by the audio receiver 11. The secondary amplifier circuit 13 is adapted for amplifying each audio signal amplified by the primary amplifier circuit 11. The current amplifier circuit 14 is adapted for processing each output audio signal of the secondary amplifier circuit 13 into an audio signal below 79 db (equal to 1V voltage) for output. The wave detection circuit 15 is adapted for receiving each output audio signal of the current amplifier circuit 14 and processing it into an audio signal below 1V (below 79 db) for output. The switch circuit 16 can be a transistor or diode. The switch circuit 16 is switched on when received a voltage below 1V from the wave detection circuit 15, allowing the amplified audio signal outputted by the primary amplifier 12 to pass through the switch circuit 16. The regulator circuit 17 is a variable resistor operable to control the sound volume of the audio signal passed through the switch circuit 16.

The Bluetooth module 2 comprises an antenna 21, a Bluetooth microphone 22, and a volume control circuit 23 formed of a variable resistor. The Bluetooth module 2 is electrically coupled with a left channel mixer 31 and a right channel mixer 32 of the audio mixer unit 3. The Bluetooth module 2 receives and processes signals from a mobile communication device (not shown) through the antenna 21, and outputs the processed signals through the left channel mixer 31 and the right channel mixer 32, enabling the user to hear voices from a remote site or to listen to the music transmitted by the mobile communication device. The voices of the user are received by the Bluetooth microphone 22, and then processed by the Bluetooth module 2 and transmitted to the mobile communication device wirelessly by the antenna 21.

As stated above, the audio mixer unit 3 consists of the aforesaid left channel mixer 31 and right channel mixer 32. The audio signals outputted by the audio signal processor unit 1 and the Bluetooth module 2 are respectively inputted into the left channel mixer 31 and the right channel mixer 32.

The amplifier unit 4 consists of a left audio amplifier circuit 41 and a right audio amplifier circuit 42, and is adapted for receiving and processing the output audio signals of the audio mixer unit 3 and outputting the processed audio signals into left and right speakers (not shown).

Figure 2:
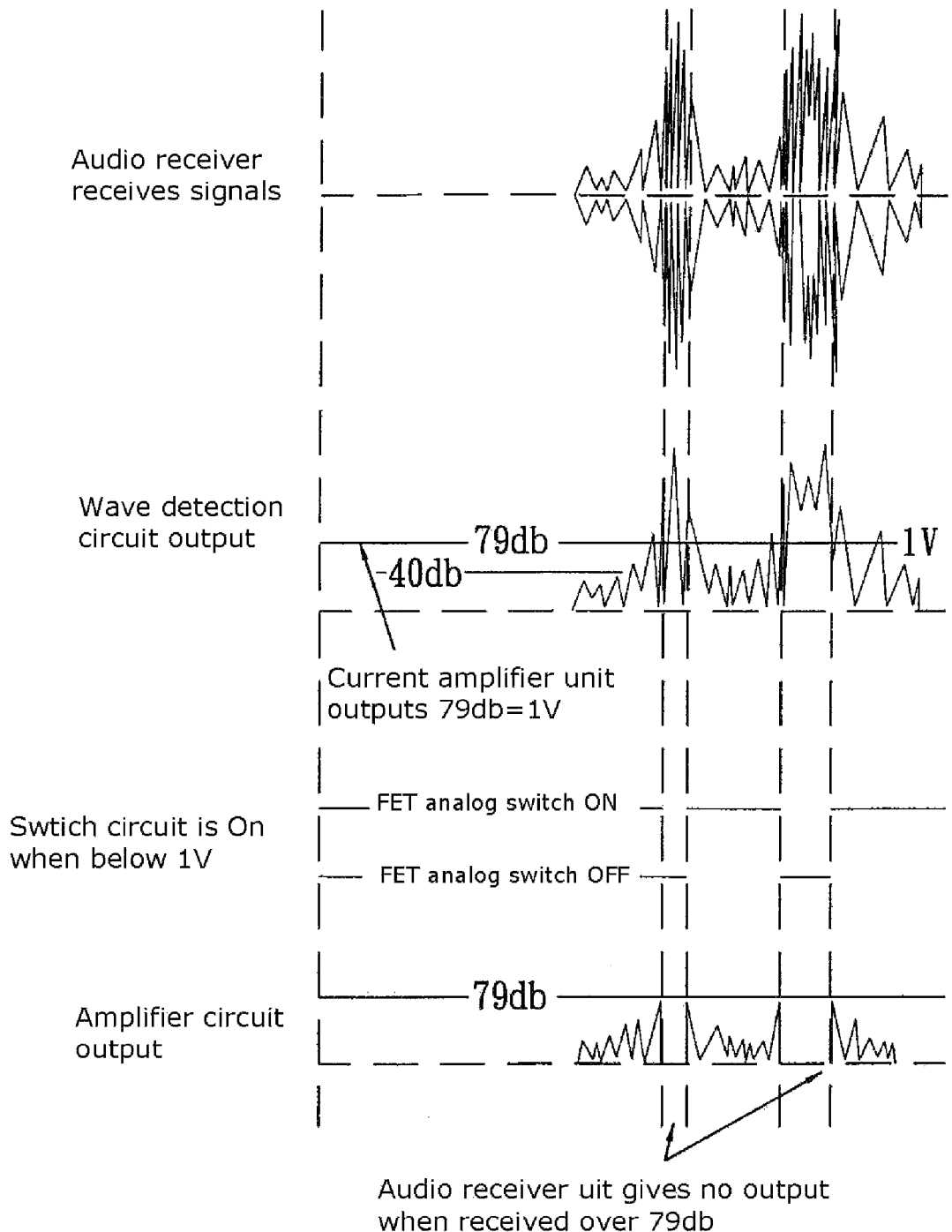
FIG. 2 is a schematic drawing illustrating the waveforms produced by the circuits of the audio signal processor of the anti-noise earmuff device in accordance with the first embodiment of the present invention.

Referring to FIG. 2 and FIG. 1 again, when the shooter (user) starts shooting, the audio receiver 11 picks up external audio signals and outputs the received audio signals to the primary amplifier circuit 12 for amplification. The audio signals amplified by the primary amplifier circuit 12. The amplified audio signals outputted by the primary amplifier circuit 12 are then properly processed through the secondary amplifier circuit 13, the current amplifier circuit 14 and the wave detection circuit 15. If the voltage of any audio signal outputted by the wave detection circuit 15 is greater than 1V, the switch circuit 16 is off, and the audio signal amplified by the primary amplifier circuit 12 is prohibited from passing through the switch circuit 16. If the voltage of any audio signal outputted by the wave detection circuit 15 is below 1V, the switch circuit 16 is on, and the audio signal amplified by the primary amplifier circuit 12 is allowed to pass through the switch circuit 16 to the regulator circuit 17 and then the audio mixer unit 3 and the amplifier unit 4 for further processing and output to the speakers so that the user can hear the audio signals received by the audio signal processor unit 1. Thus, no noise of high-decibel level is allowed to pass through the speakers, and the earmuff devices well protect the user's eardrums.

Further, by means of the Bluetooth module 2 to receive music from the mobile communication device or to communicate with the mobile communication device, the user can communicate with people outside or to listen to the music without needing taking off the earmuff device.

Figure 3:
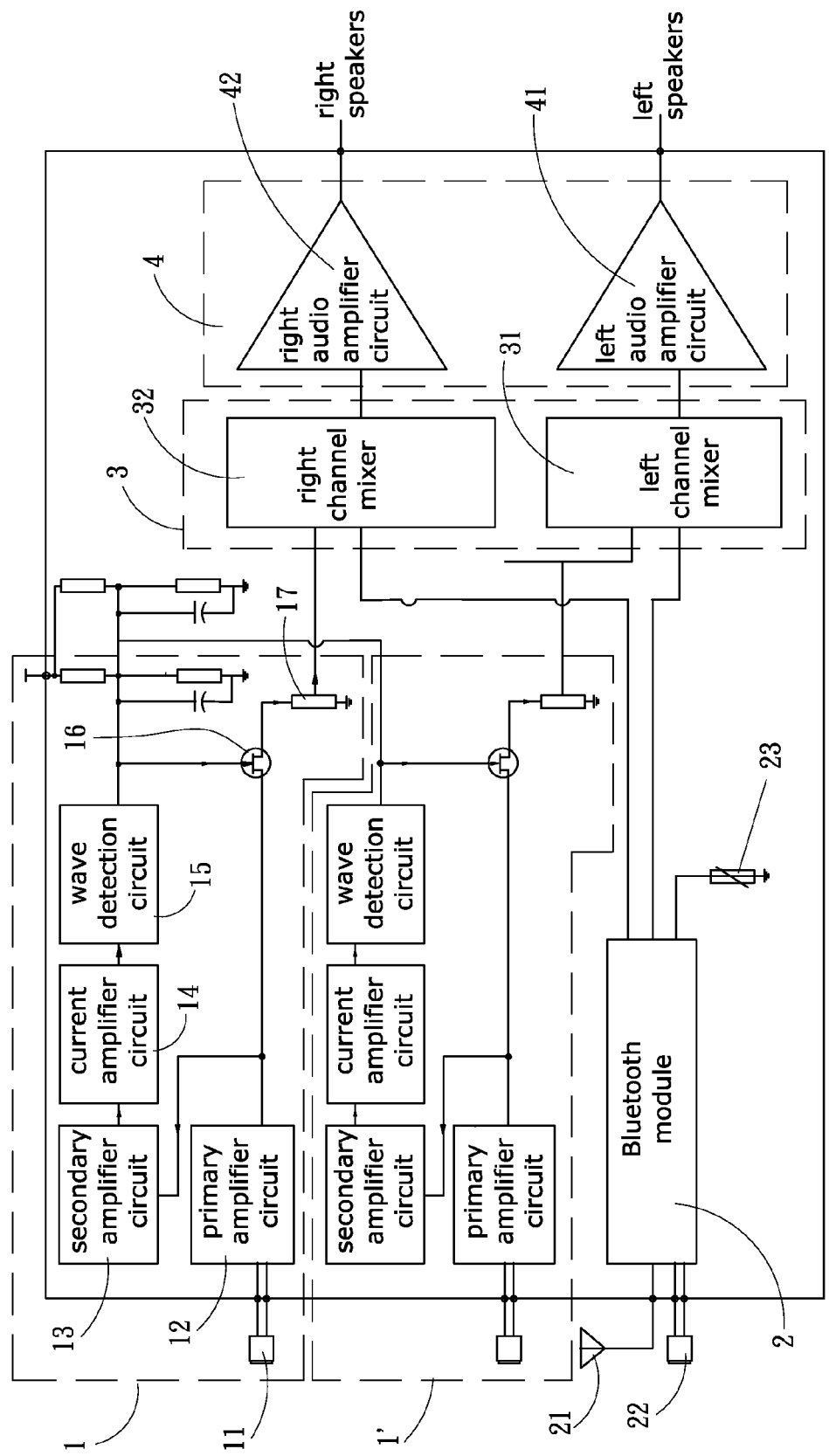
FIG. 3 is a system block diagram of an anti-noise earmuff device in accordance with a second embodiment of the present invention.

FIG. 3 illustrates an anti-noise earmuff device in accordance with a second embodiment of the present invention. This second embodiment is substantially similar to the aforesaid first embodiment with the exception of the added audio signal processor 1' to isolate external noises of high-decibel level or audio signals of high-decibel level received from different directions, and to generate a stereo sound effect.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:

1. An anti-noise earmuff device, comprising:
at least one audio signal processor unit adapted for receiving external audio signals;
said at least one audio signal processor unit reducing inputted audio signals to below 79 db;
an audio mixer unit electrically coupled with said at least one audio signal processor unit and adapted for receiving and processing the audio signals outputted by said at least one audio signal processor unit;
an amplifier unit electrically coupled with said audio mixer unit and adapted for receiving and amplifying the audio signals outputted by said audio mixer unit;
a Bluetooth module electrically coupled with said audio mixer unit;
each said audio signal processor unit consisting of an audio receiver, a primary amplifier circuit, a secondary amplifier circuit, a current amplifier circuit, a wave detection circuit, a switch circuit and a regulator circuit; and
said switch circuit of each said audio signal processor unit is selected from one of a transistor and a diode.

2. The anti-noise earmuff device as claimed in claim 1, wherein said audio receiver of each said audio signal processor unit is a capacitive microphone.

3. The anti-noise earmuff device as claimed in claim 1, wherein said regulator circuit of each said audio signal processor unit is a variable resistor.

4. The anti-noise earmuff device as claimed in claim 3, wherein said audio mixer unit consists of a left channel mixer and a right channel mixer.

5. The anti-noise earmuff device as claimed in claim 4, wherein said amplifier unit consists of a left audio amplifier and a right audio amplifier.

6. The anti-noise earmuff device as claimed in claim 4, wherein said Bluetooth module comprises a sound volume control circuit consisting of an antenna, a Bluetooth microphone and a variable resistor, and is electrically coupled with the left channel mixer and right channel mixer of said audio mixer unit.

\* \* \* \* \*